United States Patent [19]

Van Der Grift

[11] Patent Number: 5,261,546
[45] Date of Patent: Nov. 16, 1993

[54] CONTAINER FOR LIQUID OBSERVED FOR IMPURITIES

[75] Inventor: Johannes F. Van Der Grift, Schagen, Netherlands

[73] Assignee: Mallinckrodt Medical, Inc., St. Louis, Mo.

[21] Appl. No.: 729,967

[22] Filed: Jul. 15, 1991

Related U.S. Application Data

[63] Continuation of Ser. No. 459,802, May 1, 1990, abandoned.

[30] Foreign Application Priority Data

Jan. 25, 1988 [NL] Netherlands .......................... 8800154

[51] Int. Cl.$^5$ .......................................... G01N 21/90
[52] U.S. Cl. ............................... 215/12.2; 215/365; 40/310; 356/246; 356/427
[58] Field of Search ............... 215/12.1, 1 R, 365, 215/366; 40/310; 356/246, 427

[56] References Cited

U.S. PATENT DOCUMENTS

| | | | |
|---|---|---|---|
| Re. 28,984 | 9/1976 | Drinkuth et al. | 356/427 X |
| 1,570,368 | 1/1926 | Zeh | 40/310 X |
| 1,656,260 | 1/1928 | Zeh | 40/310 X |
| 2,012,127 | 8/1935 | Griffith, Jr. | 229/4.5 |
| 2,305,890 | 12/1942 | Moore | 40/310 |
| 2,368,350 | 1/1945 | Ellison | 356/427 |
| 2,646,715 | 7/1953 | Stout et al. | 356/427 |
| 2,810,978 | 10/1957 | Chapman | 215/1 R X |
| 3,207,822 | 9/1965 | Makowski | 215/365 X |
| 3,208,900 | 9/1965 | Inklaar | 40/310 |
| 3,262,492 | 11/1941 | Farrell | 40/310 X |
| 3,415,997 | 12/1968 | Vinzelberg et al. | 356/427 X |
| 3,543,241 | 11/1970 | Leuck | 40/310 X |
| 3,820,677 | 6/1974 | Garcia | 215/12.2 |
| 3,914,058 | 10/1975 | Knapp et al. | 356/197 |
| 4,021,670 | 5/1977 | Noakes | 215/200 X |
| 4,028,553 | 6/1977 | Farcinade | 356/427 X |
| 4,227,615 | 10/1980 | Flick | 215/1 C X |
| 4,402,612 | 9/1983 | Alexander et al. | 356/427 |
| 4,605,851 | 8/1986 | Ometz et al. | 356/427 X |
| 4,676,650 | 6/1987 | Bjorndal et al. | 356/427 |
| 4,684,250 | 8/1987 | Kukka et al. | 356/246 |

Primary Examiner—Sue A. Weaver
Attorney, Agent, or Firm—Rita Downard Vacca

[57] ABSTRACT

The invention relates to a substantially transparent container for liquids on one side of which are opaque light and opaque dark areas of color observable through the container for evaluating contained liquid for particulate impurities. The container is particularly useful for pharmaceutical liquids.

15 Claims, 1 Drawing Sheet

CONTAINER FOR LIQUID OBSERVED FOR IMPURITIES

This is a continuation of application Ser. No. 459,802, filed May 1, 1990, now abandoned.

FIELD OF THE INVENTION

The invention relates to a container for liquids that are evaluated for particulate impurities by visual or mechanical means.

BACKGROUND OF THE INVENTION

Many different liquids must be packaged and sealed under conditions that prevent contamination of the liquid by undesired particles. The liquids may be destined for use as reagents in analytical or diagnostic techniques requiring ultra-high purity or for administration as diagnostic or therapeutic pharmaceuticals. In preparing and packaging such liquids, extensive precautions are taken to prevent contamination by undesired particles. After preparation, the liquid is dispensed to containers which are then sealed. It is during packaging that contamination by undesired particles may occur in spite of precautions. These particles may render the liquid less valuable or inoperable for their intended purposes or may constitute a source of danger, in particular in a pharmaceutical liquid for parenteral administration to a patient. In these cases, examination of each container, after sealing, is a compulsory requirement.

Various measures have been suggested to inspect liquids dispensed in containers for the presence of undesired particles. A conventional examination method is a visual inspection which, although easy to perform and sufficiently reliable, is rather time-consuming. In such an inspection, the liquid is preferably illuminated with an artificial light source, either directly or indirectly. The filled containers, after the liquid has been put in motion, usually are held successively against a black and a white background, so that light-colored and dark-colored particles, if any, in the liquid become visible. In such an inspection, it is desirable to keep the inspection time per container as short as possible, without compromising the reliability of detection, merely for economic reasons. However, shortening of the time necessary for inspection is of prime importance when viewing or visually inspecting containers having a radioactive liquid for reasons of safety. Although the observer's eye is protected as well as possible during viewing from radiation by, for example, positioning a transparent shield of lead-glass between the observer and the container to be inspected, it cannot be entirely prevented. So the exposure time, i.e., the time in which the observer is exposed to radiation from the container, must be minimized.

In another usual method of inspecting liquids dispensed in containers for the presence of undesired particles, suitable illuminating means and a detection apparatus are used. By illuminating the liquid in the container in a special manner with the light of a carefully selected light source and then determining the intensity of the transmitted or scattered light by means of, for example, a photosensitive cell, a camera or a video camera with display screen, an impression can be gained about the extent to which the liquid has been contaminated with particles. Such an inspection device is disclosed in U.S. Pat. No. 4,676,650.

These and similar devices are not only complex and hence sensitive to disturbances, and expensive as regards acquisition and maintenance, but they are also not always satisfactory with regard to reliability and detection sensitivity.

It is the object of the present invention to provide a more simple and reliable means of examining liquids for impurities which can be used universally, i.e., both for visual inspection and for use with detection apparatus, and by which the examination can be facilitated so that the inspection time can be shortened as compared with the known visual inspection methods.

It is a further object to provide the means to more easily inspect liquids some time after packaging for changes such as sedimentation, crystalization, or gelling.

SUMMARY OF THE INVENTION

The present invention meets the above described objects by providing contrasting dark and light colored backgrounds against which a liquid is observed by applying to or incorporating in the container opaque areas of color. This is accomplished by adding the colored areas to a part of a side of a substantially transparent container for the liquid. The advantage of this invention lies in that a single observation will detect both light and dark particulate impurities and in that light beam distortion through curved walls is avoided.

Figure 1:
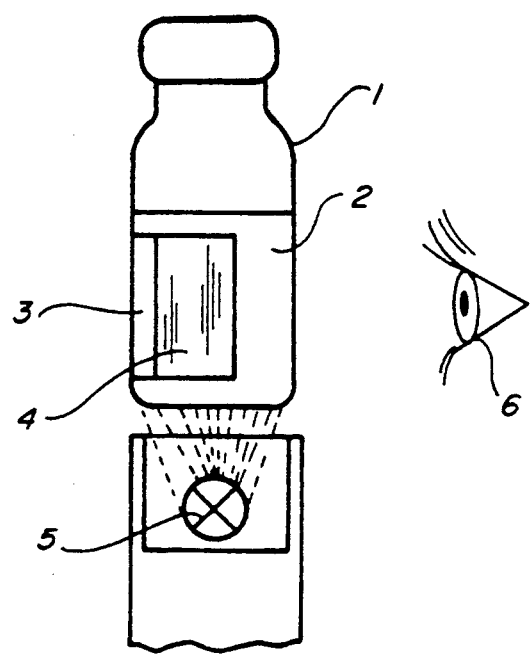
FIG. 1 is a side view of a container according to the invention.

Reference numeral 1 in the drawing denotes a sealed vial which contains a liquid 2. The wall of the vial comprises a rectangular area which is partly white 3 and black 4 and which has been provided in the glass wall by ceramic fusion printing. For inspection of the liquid the vial is illuminated with the light of a light source 5 through the flat bottom, the light source being positioned beneath the vial. The place of the observer's eye 6 is also shown in the drawing.

DETAILED DESCRIPTION OF THE INVENTION

The invention is a container which provides the means of observing contained liquid for particulate impurities. The container is composed of substantially transparent material for its side wall or walls. It may also have a transparent bottom. Opaque, contrasting areas of color are provided on a part of a side wall. Preferably one white area and one black area are provided. They are preferably rectangular in shape and immediately adjacent to one another.

The areas of color may cover a varying portion of the side area of the container. There must be a portion left transparent for the observation to be made, but the minimum and maximum limits and the preferred total area of color may vary for different forms and sizes of containers. The means of observation to be used will also be determinative. For a cylindrical container a preferred configuration is to cover one half of the side wall with color, half of the area being a light rectangle and half being a dark rectangle, more preferably being white and black, respectively.

The areas of color may be provided in a number of ways. For example, a label may be placed on the outside of the container which has the color areas printed on the reverse side, thereby visible through the container. Permanent application to the container may be made by fusing the color to the side wall, preferably to the exterior of the container. The colored areas are then not liable to be removed, damaged or become dirty during handling and filling. This fusing may be accomplished by etching or ceramic fusion printing, for example.

Labelling over the colored areas may then be made either before or after inspection. Problems with identification of the contents of the container are prevented by an early labelling. By providing the label over the contrasting color areas, the field of sight during the inspection is not limited, nor does the necessity exist of inspecting the contents of the container at a given angle with the possibility of annoying reflections at the glass.

The container must be substantialy transparent through the remainder of the side wall or walls, and preferably through the bottom. It may be composed of a variety of materials, chosen for compatibility with the contained liquid and other reasons such as cost. Glass is a preferred container composition for pharmaceutical liquids.

The shape of the container is chosen according to the function and properties of the liquid. Examples of suitable container shapes are vials, ampules, bottles, and test tubes. However, the conformation of the container is not limited by the present invention, only by the characteristics and use of the contained liquid.

The advantages of the container having contrasting color areas according to the invention become most prominent during use, that is, when the container has been filled with a liquid and closed or sealed. For inspecting the contents for the presence of undesired particles, the liquid is put in motion and the container, with the colored area to the rear, is placed at eye level of the observer or at the level of the detection apparatus used, while the liquid is illuminated, preferably through the bottom of the container, that is, perpendicular to the direction of observation. Such an illumination through a preferably flat bottom leads to sharper light beams and clearer scattering by the particles, while annoying reflections in the case of light through the curved wall are avoided. As a result of this the quality of the evaluation, both after visual and after instrumental observation, is improved. The contrasting dark and light colored areas serve as a background for the liquid to be inspected. As the background is present nearer to the liquid, the contrast between the dark and the light background is sharper. This improves the quality of the observation as compared with the known method in which the container is held successively against a black background and a white background. In addition, when using a container according to the invention, displacement or rotation of the container during the inspection to enable inspection of the contents thereof against a varying background may no longer be necessary. As a result of this, fewer operations are required so that the inspection time is reduced. In visual observation, the eye gets tired less rapidly, while in instrumental observation the detection apparatus need not be refocused again and again.

It will be obvious from the above that, compared with known containers not providing contrasting dark and light colored areas, the container according to the invention provides for a simple and reliable inspection that is facilitated so that the time required can be reduced. In addition to visual inspection, the container according to the invention is also suited, as indicated hereinbefore, for instrumental observation, in which photoelectric, photographic or video techniques may be used. The results thus detected can, of course, be processed by means of modern techniques, for example, by means of a computer.

I claim:

1. A container for a radiopharmaceutical liquid designed to allow for easy examination for multicolored, particulate impurities in said radiopharmaceutical liquid, comprising a container having a substantially transparent side and bottom part of said side having contrasting areas of color dimensioned to block passage of light and show multicolored impurities present in said radiopharmaceutical liquid, whereby exposure to said radiopharmaceutical liquid during an examination is minimized.

2. A container according to claim 1, wherein said container has a transparent bottom.

3. A container according to claim 2, wherein said bottom is substantially flat.

4. A container according to claim 2, wherein said bottom and a part of said side are transparent glass.

5. A container according to claim 2, wherein said bottom and a part of said side are transparent plastic.

6. A container according to claim 2, wherein said contrasting areas of color are white and black.

7. A container according to claim 6, wherein said contrasting areas of color are rectangular in shape.

8. A container according to claim 2, wherein an exterior label is applied to said container to provide said contrasting areas of color whereby said exterior label is visible through an opposing side surface to show multicolored impurities.

9. A container according to claim 2, wherein said container is a vial for pharmaceuticals.

10. A container according to claim 1 wherein said contrasting areas of color are fused to said side.

11. A container according to claim 10, wherein said contrasting areas of color are etched on said side.

12. A container according to claim 10, wherein said contrasting areas of color are fusion printed on said side.

13. A container according to claim 10, further comprising a label which covers said contrasting areas of color.

14. A container for a radiopharmaceutical liquid designed to allow for easy examination for multicolored, particulate impurities in said radiopharmaceutical liquid, comprising a container having a substantially transparent side and bottom, part of said side having contrasting areas of color dimensioned to block passage of light to show multicolored impurities present in said radiopharmaceutical liquid.

15. A container for a radiopharmaceutical liquid comprising a transparent container, and contrasting areas of color thereon dimensioned to simplify.

* * * * *